United States Patent [19]

Linderborg

[11] Patent Number: 4,585,795

[45] Date of Patent: Apr. 29, 1986

[54] CONTROL AGENT FOR PROTECTING TIMBER AGAINST FUNGI EMPLOYING A MIXTURE OF AN ORGANIC CARBOXYLIC ACID SALT AND QUATERNARY AMMONIUM SALT

[75] Inventor: Irma Linderborg, Kuusankoski, Finland

[73] Assignee: Kymi Kymmeno Oy, Helsinki, Finland

[21] Appl. No.: 726,299

[22] Filed: Apr. 24, 1985

Related U.S. Application Data

[63] Continuation-in-part of Ser. No. 475,769, Mar. 16, 1983, abandoned.

[30] Foreign Application Priority Data

Mar. 19, 1982 [FI] Finland ................................. 820968
Feb. 3, 1983 [FI] Finland ................................. 830374

[51] Int. Cl.$^4$ ............................................. A01N 37/00
[52] U.S. Cl. ....................................... 514/558; 514/557
[58] Field of Search ........................ 514/558, 557, 642

[56] References Cited

U.S. PATENT DOCUMENTS 3,565,927  2/1971  Wakeman et al. ................... 260/404
4,061,500  12/1977 Hager ................................. 106/15 R
4,380,561  4/1983  Sundman et al. .................... 427/421

OTHER PUBLICATIONS

Butcher et al., "Efficacy of Acidic and Alkaline Solutions of Alkylammonium Compounds as Wood Preservatives", *N.Z.J. For Sci.*, 8(3):403-9 (1978).
Hulme et al., "Control of Fungal Sap Stain with Alkaline Solutions of Quaternary Ammonium Compounds and with Tertiary Amine Salts", *Forest Product Journal*, vol. 29, No. 11, pp. 26-29 (1979).
B. A. Richardson, "Sapstain Control", Paperi ja Puu, No. 10, pp. 613-624 (1972).
Onions et al, "Smith's Introduction to Industrial Mycology", (Edward Arnold Ltd), pp. 340-341 (1981).
Block, "Disinfection, Sterilization and Preservation" (Lea & Febiger) pp. 813, 922 (1983).
Wessels et al., "Some Data on the Relationship Between Fungicidal Protections and pH", p. 517 (undated).
Walters et al., *Biodeterioration of Materials*, pp. 517-523 (1968).

*Primary Examiner*—Allen J. Robinson
*Attorney, Agent, or Firm*—Wood, Dalton, Phillips, Mason & Rowe

[57] ABSTRACT

A control agent composition for protecting timber against fungi which cause sapstain and mildew is disclosed. It contains as a synergistic mixture an alkali metal salt of some biocidal organic acid and one or several quaternary ammonium salts belonging to the group of monoalkyltrimethyl-, dialkyldimethyl- and alkylaryldimethylammonium chlorides and alkylpyridinium chlorides. In the molecules of these the alkyl groups contain 8–18 C atoms.

3 Claims, No Drawings

CONTROL AGENT FOR PROTECTING TIMBER AGAINST FUNGI EMPLOYING A MIXTURE OF AN ORGANIC CARBOXYLIC ACID SALT AND QUATERNARY AMMONIUM SALT

CROSS REFERENCE TO RELATED APPLICATION

This application is a continuation-in-part of copending, commonly assigned application Ser. No. 475,769 filed Mar. 16, 1983, now abandoned.

BACKGROUND OF THE INVENTION

The present invention relates to a control agent composition for short-term protection of timber against sapstain fungi and mildews.

The fungi which deteriorates timber are classified into three categories:
1: Sapstain fungi
2: Mildews
3: Decay fungi Sapstain fungi cause detrimental dark spots in timber, if they are growing in it. However, they do not decay or weaken timber, but their presence can later accelerate the growth of actual decay fungi (Basidiomycetes). The same can be said about ordinary mildew fungi, the colored spores of which can spoil the appearance of timber. Protection against sapstain and against growth of mildew can be achieved in a relatively simple manner: by immersing the timber in a control agent, by spraying the timber or by brushing on the agent, whereas anti-rot treatment requires impregnation under pressure in order to achieve protection down to a deeper level.

The agents most commonly used so far for preventing sap-stain contain penta- and tetrachlorphenols as the active ingredient, or sodium salts of these. However, their use is no longer desirable owing to their assumed hazard to workers and their environmental effects. For this reason it is necessary to develop an effective control agent which is harmless in the above-mentioned respects. A control agent working well should also be completely soluble in water, since the stability of emulsions and suspensions is limited, and the various phases may separate at the timber treatment stage. Also, it must not stain the timber or complicate further treatment of the timber. The agent should also adhere so well to the timber surface that it is not washed off by, for example, rain.

The object of the present invention is to provide such a well working, harmless agent for protecting timber.

SUMMARY OF THE INVENTION

According to the present invention there is provided a control agent composition for protecting timber, especially sawn timber, against fungi which cause sapstain and mildew, which composition contains as a synergistic mixture an alkali metal salt of some biocidal organic carboxylic acid which contains C, H and O atoms and one or several quaternary ammonium salts belonging to the group of monoalkyltri-methyl-, dialkyldimethyl- and alkylaryldimethylammonium chlorides and alkylpyridinium chlorides, in the molecules of which the alkyl groups contain 8–18 C atoms.

DESCRIPTION OF THE PREFERRED EMBODIMENTS

The present invention thus relates to the use of synergistic mixtures of quaternary ammonium salts and of fungistatic sodium salts of organic carboxylic acids which contain C, H and O atoms, especially aliphatic acids, also branched fatty acids, as control agents, whereby a better efficacy is achieved than by using the said compounds alone. The quaternary ammonium salts which can be used include especially those belonging to the monoalkyltri-methyl-, dialkyldimethyl- and alkylaryldimethylammonium salts, but the salts of quaternarized pyridine are also usable. These compounds can be used either alone or in the form of mixtures.

In a preferred embodiment of the present invention the organic acid contained in the synergistic mixture is a fungistatic aliphatic, straight-chain or branched carboxylic acid having 6–12 C atoms. Typically the organic acid contained in the synergistic mixture may also be an acetylsalisylic acid, benzoic acid or sorbic acid. The branched, aliphatic carboxylic acid contained in the synergistic mixture again is preferably 2-ethyl hexanoic acid. The main constituent of the quaternary ammonium salts contained in the present synergistic mixture is preferably dodecylbenzyldimethylammonium chloride or tetradecylbenzyldimethyl-ammonium chloride.

Quaternary ammonium salts are previously known control agents used for protecting timber [B. A. Richardson; Sapstain Control, Paperi ja Puu No. 10, p. 613 (1972)], as are aliphatic, straight-chain carboxylic acids having 6–11 C atoms in their carbon chain [Hager AB (Häger, B. O.) Finnish Patent Application No. 752676 B 27 K]. Branched aliphatic carboxylic acids, e.g. 2-ethyl hexanoic acid [KenoGard AB (Sundman, Hägglund) Finnish Patent Application No. 811283 B 27 K prior. SE 28.4.1980 8003219-6], also act on sapstain fungi. Benzoic and sorbic acids or acetylsalisylic acid, for example, can be used as anti-mildew agents. However, it is known that the action of the said agents is dependent on the pH (Seymour B. Block, Disinfection, Sterilization and Preservation, p. 914, Lea & Febiger Philadelphia, 1977 2 p). Organic acids have a better efficacy only when pH has fallen to such a value that there is a sufficient amount of the undissociated form present. When this is so, the acids are, however, less readily soluble. The efficacy of quaternary ammonium salts, on the other hand, is better when the pH is $\geq 7.0$. The pH of timber surface usually varies between 3.5 and 7.0, depending on the species (A. Harry Walters and John J. Elphick, Biodeterioration of Materials, p. 617, Elsevier Publ. Co Ltd, 1968, London). Since pH on the surface of timber tends gradually to drop under the action of the acids of the wood, it is advantageous to use a mixture of a quaternary compound and an acid, whereby a higher effective pH range is achieved. However, the initial pH of the control agent in question must, of course, be so high that the acid is in the form of a sodium salt in the solution, in which case it is water soluble. If so desired, some buffering agent, e.g. boric acid, borax or soda, can be added to the control agent, to maintain the pH of the solution constant during the treatment stage. The use of borium compounds also increases the efficacy of the preparation, since they are known to be fungitoxic (A. H. S. Onions, D. Allsopp, H. O. W. Eggins, Smith's Introduction to Industrial Mycology, p. 341, Edward Arnold Ltd 1981). The suitable pH is 7–10. When the pH later drops, organic acid is released from the control agent and precipitates on the surface of the timber. This improves the efficacy of the treatment. It also increases the weather resistance of the timber. In order to serve the purpose, the organic acid used as a control agent should be at least 50% dissociated within the pH range in question, i.e. its pKa constant should be $\geq 4-5$. The dissociation constants of certain known organic acids used as control agents are given in the following table.

|  | pKa |
| --- | --- |
| Capric acid | 4.9–5.0 |
| Capronic acid | 4.83 |
| 2-ethyl hexanoic acid | 4.81 |
| Sorbic acid | 4.77 |
| Benzoic acid | 4.19 |
| Acetylsalicylic acid | 3.27 |

It has now been oberved surprisingly that the studied quaternary ammonium salt and organic acids increase the fungitoxicity of each other synergistically. This effect is especially clear specifically within a pH range of $\leq 5.0$, which can be used in the protection of timber. The phenomenon is most likely based on the cell-membrane damaging action of quaternary compounds, in which case the acid can penetrate the cell more easily. This was shown by the laboratory experiments which are described in the following examples.

It has not been observed that the control agents according to the invention would stain timber or complicate its painting, for example.

Laboratory experiments were carried out by making (1) dish cultures with Czapek-Dox agar at a temperature of 23° C. and (2) mini-board tests at a temperature of 23° C. and a humidity of 100%. The dish cultures had been inoculated with spores of the fungus *Aureobasidium pullulans.* This is a known fungus causing sapstain. In the mini-board tests, the inoculation was carried out using a spore suspension which contained a mixture of the spores of sapstain fungi. The sapstain fungi used were *Aureobasidium pullulans, Sclerophoma entoxylina* and *Ceratocystis pilifera.*

The toxic effect of the substances studied was observed preliminarily in the dish cultures. In the mini-board tests it was studied whether the toxic effect is retained on the surface of timber. The dimensions of the mini-boards were $10 \times 50 \times 300$ mm. They had been made from newly felled pine. The pieces were immersed for 20 s into the solutions studied and were then weighed and inoculated. The control pieces were immersed into pure water. Some of the test pieces were dried for 1 month at 23° C. at a humidity of 100% in dishes covered with a plastic sheet, whereafter the sapstain and the mildew growth in them were assessed visually.

EXAMPLE 1

In dish cultures with *A. pullulans* fungus it was observed that growth was inhibited at, for example, the following concentrations of the control agents studied within a culture period of 15 days:

| Control agent studied | pH 2.5 | pH 5.0 | pH 7.0 |
| --- | --- | --- | --- |
|  | ←ppm→ | | |
| BAC | 50 | 10 | 2 |
| DMC | 15 | 15 | 4 |
| 2-ethyl hexanoic acid | 50 | >100 | >1000 |
| Capric acid | 50 | 100 | >>100 |
| Sorbic acid | 50 | 100 | >>100 |
| Acetylsalicylic acid | 25 | >100 | >1000 |

-continued

| Control agent studied | pH 2.5 | pH 5.0 | pH 7.0 |
| --- | --- | --- | --- |
|  | ←ppm→ | | |
| Benzoic acid | 50 | >100 | >>100 |

Using certain mixtures of these control agents, fungus growth could be inhibited at the following concentrations, for example:

| Control agent studied | pH 2.5 | pH 5.0 | pH 7.0 |
| --- | --- | --- | --- |
|  | ←ppm→ | | |
| (1) BAC + capric acid | 15:15 | 2:5 | 2:5 |
| (2) BAC + sorbic acid |  | 2:5 | 2:5 |
| (3) BAC + acetylsalisylic acid | 10:10 | 5:10 | 2:5 |
| (4) BAC + 2-ethyl hexanoic acid |  | 5:10 | 2:5 |
| (5) DMC + 2-ethyl hexanoic acid |  | 5:10 | 2:5 |
| (6) DMC + acetylsalisylic acid | 5:10 | 5:10 | 2:5 |
| (7) DMC + capric acid | 5:10 | 5:10 | 2:5 |
| (8) DMC + sorbic acid |  | 2:5 | 2:5 |

Thus, in general the effect obtained using mixtures of agents was better than that obtained using the original constituents alone.

Explanation of the abbreviations:
BAC=dodecylbenzyldimethylammonium chloride
DPC=dodecylpyridinium chloride
DMC=dodecyltrimethylammonium chloride ($C_{12}$-90%)

EXAMPLE 2

The following results were obtained in tests carried out using the above-mentioned spore suspension of sapstain fungi in mini-board tests on fresh timber at 23° C. and at a humidity of 100% within a test period of 1 month:

| Control agent studied | Concentration of active ingredient in wetting solution % | Grading points | |
| --- | --- | --- | --- |
|  |  | Sapstain | Surface mildew |
| BAC | 1.2 | 2 | 8.5 |
|  |  | 1.5 | 4.5 |
| DMC | 1.2 | 1 | 16 |
|  |  | 1 | 7 |
| DPC | 1.2 | 3 | 16 |
| 2-ethyl hexanoic acid | 1.2 | 0.5 | 18 |
|  |  | 6.5 | 7.5 |
| Capric acid | 1.2 | 3.5 | 14 |
| Mixture of BAC and 2-ethyl hexanoic acid (1:2) | 1.2 | 0 | 3 |
|  |  | 0 | 1.5 |
| Mixture of DMC and 2-ethyl hexanoic acid (1:2) | 1.2 | 0 | 2.5 |
|  |  | 0 | 2.5 |
| Mixture of DPC and 2-ethyl hexanoic acid (1:2) | 1.2 | 0 | 2.5 |
|  |  |  | 1.5 |
| A commercial timber-protection agent | 1.2 | 3 | 17 |
|  |  | 0.5 | 8.5 |
| 0-test | — | 13 | 13 |
|  |  | 16 | 16 |

The pH of the wetting solutions was adjusted to 8.4.

These test results also show a clear improvement in the efficacy as regards both sapstain and surface mildew, when the control agent was a mixture of a quaternary ammonium salt and an organic acid. Another reason why it is not advantageous to use the constituents of the mixtures alone is that when there is an excessive growth of surface mildew.

The moisture absorbed into the mini-boards was usually 3-4 g.

System of grading:
0-5 points=very good
6-10 points=average
11-15 points=poor
16-20 points=very poor

EXAMPLE 3

A mini-board experiment carried out using the above-mentioned spore suspension of sapstain fungi in the same way as in Example 2, the control agent containing varying concentrations of technical dodecylbenzyl-dimethylammonium chloride (BAC) and Na salt of 2-ethyl hexanoic acid (2-EHA-Na) yielded the following results:

| Test No. | Concentrations of control agent | | Concentration of wetting solution % | Grade points | | | |
|---|---|---|---|---|---|---|---|
| | BAC* % | 2-EHA-Na % | | Sapstain | | Surface mildew | |
| | | | | Fresh timber | Dried timber | Fresh timber | Dried timber |
| 1 | 8.2 | 91.8 | 1.5 | 0.5 | 0 | 8.5 | 1 |
| 2 | 15.6 | 84.4 | 1.6 | 1.5 | 0 | 2.5 | 3 |
| 3 | 21.0 | 79.0 | 1.4 | 1 | 0 | 3.5 | 3 |
| 4 | 28.6 | 71.4 | 1.4 | 0 | 0 | 0 | 7.5 |
| 5 | 35.7 | 64.3 | 1.8 | 0 | 0 | 0 | 1 |
| 6 | 45.5 | 54.5 | 1.8 | 0 | 0 | 0 | 1 |
| 0-test | — | — | — | 9 | 1.5 | 15 | 18 |

*Technical BAC also contains a certain amount of $C_{14}$—alkyl groups.

Grading system as in Example 2.

Thus, for complete inhibition of sapstain it was sufficient to wet the timber in a 1.4% solution which contained 28.6% dodecylbenzyldimethylammonium chloride and 71.4% Na salt of 2-ethyl hexanoic acid. When necessary, a stronger solution can be used for controlling surface mildew, for example a 1.8% solution which contains relatively more, e.g. 35% dodecylbenzyldimethylammonium chloride. The concentration of the treatment solution can, of course, be increased even further to a level of 2.5-5.0%, depending on the use and on cost factors. A 2.5% solution which contains 33% technical dodecylbenzyldimethylammonium chloride and 67% Na salt of 2-ethyl hexanoic acid is likely to be usable in most cases.

EXAMPLE 4

The control agent composition presented in Test 4 of Example 3 was modified in such a way that part of the dodecylbenzyldimethylammonium chloride was replaced with technical dialkyldimethylammonium chloride which contained, bound with nitrogen, $C_8$–$C_{18}$ alkyl groups as follows: $C_{18}$-8%, $C_{10}$-9%, $C_{12}$-47%, $C_{14}$-18%, $C_{16}$-8% and $C_{18}$-10%.

A mini-board experiment carried out using mixtures of these quaternary compounds and Na salt of 2-ethyl hexanoic acid yielded the following results:

| Test No. | $C_8$-$C_{18}$ quaternary ammonium chloride % of total amount of ammonium salts | Total amount of quaternary ammonium chlorides % (dry matter) | Na salt of 2-ethyl hexanoic acid % (dry matter) | Total dry Matter % | Grade points Dried timber | |
|---|---|---|---|---|---|---|
| | | | | | Sapstain | Surface mildew |
| 1 | 50.0 | 28.6 | 71.4 | 1.4 | 0 | 4 |
| 2 | 25.0 | 28.6 | 71.4 | 1.4 | 0 | 3 |
| 3 | 22.1 | 60.6 | 39.4 | 1.4 | 0 | 3.5 |
| 4 | 25.0 | 67.0 | 33.0 | 2.5 | 0 | 0 |

If the results of Tests 1-3 are compared with Test 4 of previous Table 3, which had the same dry matter content, the result improved clearly as regards the inhibition of surface mildew growth. Thus a 1.4% solution already provided a rather good protection against mildew in this case.

EXAMPLE 5

One side of each of the mini-boards was immersed into a control agent solution which contained didecyl-dimethyl-ammonium chloride (DDC) and Na salt of 2-ethyl hexanoic acid. The concentration of the solution was 2.5%. The immersion period was 20 s. The boards were allowed to drip, and they were inoculated with the above-mentioned spore suspension of sapstain fungi. The boards were stored at a humidity of 100% at a temperature of 23° C. for 3 weeks, whereafter they were inspected, and the following results were obtained:

| Test No. | Solution No. | Concentration of control agent, % of dry matter of wetting solution | | Dry matter of wetting solution % | Grade points Sapstain | |
|---|---|---|---|---|---|---|
| | | DDC | 2-EHA-Na | | Treated side | Untreated side |
| 1 | 1 | — | 100 | 1.5 | 20 | 20 |
| | 2 | 10 | 90 | 1.5 | 6 | 16 |
| | 3 | 33.5 | 66.5 | 1.5 | 6 | 19 |
| | 4 | 66.5 | 33.5 | 1.5 | 7 | 20 |
| | 5 | 100 | — | 1.5 | 12 | 20 |
| 2 | 1 | — | 100 | 2.5 | 16 | 20 |
| | 2 | 10 | 90 | 2.5 | 8 | 20 |
| | 3 | 33.5 | 66.5 | 2.5 | 0 | 18 |
| | 4 | 66.5 | 33.5 | 2.5 | 1 | 19 |
| | 5 | 100 | — | 2.5 | 5 | 20 |

The results show that the best protection against sapstain was obtained using solutions which contained 33.5-66.5% didecyldimethylammonium chloride and 66.5-33.5% Na salt of 2-ethyl hexanoic acid. The constituents used alone were less effective.

EXAMPLE 6

The following experiment was carried out as in Example 5, but a suspension of spores of the mildew fungi listed below was used for the inoculations:
*Cladosporium sphaerospermum*
Penicillum Sp.
*Aspergillus amstelodami*
The results are shown in the following table:

| Solution No. | Control agent concentration, % of dry matter of wetting solution | | Dry matter of wetting solution % | Grade points Mildew growth | |
|---|---|---|---|---|---|
| | DDC | 2-EHA-Na | | Treated side | Untreated side |
| 1 | — | 100 | 1.5 | 20 | 20 |
| 2 | 10 | 90 | 1.5 | 13 | 20 |
| 3 | 33.5 | 66.5 | 1.5 | 8 | 19 |
| 4 | 66.5 | 33.5 | 1.5 | 5 | 20 |
| 5 | 100.0 | — | 1.5 | 11 | 20 |

The control agent composition also checked mildew fungus growth, especially within the concentration ranges of 33.5–66.5% DDC and 66.5–33.5% 2-EHA-Na. The constituents of the composition used alone were less effective in this case also.

EXAMPLE 7

Wetting tests were carried out at sawmills by using control agent solutions which contained 66.5% Na salt of 2-ethyl hexanoic acid and 33.5% either dimethyl-coco-benzylammonium chloride in which the distribution of the alkyl chains is $C_8$ 7%, $C_{10}$ 7%, $C_{12}$ 50%, $C_{14}$ 21%, $C_{16}$ 9%, $C_{18}$ 6% (Solution 1) or trimethylcocoammonium chloride in which the distribution of alkyl chains is $C_8$ 7%, $C_{10}$ 7%, $C_{12}$ 49%, $C_{14}$ 22%, $C_{16}$ 9%, $C_{18}$ 6% (Solution 2). In this experiment, 50% of the boards were dried before storing. The pH of the wetting solutions was adjusted to 9.3. In one test, 1% boric acid was added to the wetting solution in order to increase the buffer capacity of the solution (Solution $2^x$).

The boards were stored outdoors during September–November for 2½ months, whereafter they were inspected, and the following results were obtained:

| Control Agent | Concentration % | Average degree of deterioration (0–4) | | | |
|---|---|---|---|---|---|
| | | Sawmill 1 | | Sawmill 2 | |
| | | Fresh | Dried | Fresh | Dried |
| Solution 1 | 2.5 | 0.62 | 0.04 | 0.14 | 0.02 |
| Solution 2 | 1.5 | 1.74 | 0.02 | 0.18 | 0.02 |
| Solution 2 | 2.5 | 0.24 | 0.00 | 0.10 | 0.00 |
| Solution $2^x$ | 1.5 (cont. 1% boric acid) | 0.42 | 0.02 | 0.00 | 0.02 |
| A commercial timber protection agent | 2.5 | 2.66 | 0.24 | 0.54 | 0.04 |
| Reference | — | 3.22 | 0.16 | 2.90 | 0.04 |

The results show that Solutions 1 and 2 having a dry matter concentration of 2.5% protected timber quite well, and that the efficacy of 1.5% Solution 2 improved considerably when 1% boric acid had been added to it (Solution $2^x$). Its pH remained steady, as can be seen from the following table:

| Control agent | Concentration % | pH before wetting | pH after wetting |
|---|---|---|---|
| Solution 1 | 2.5 | 9.3 | 9.1 |
| 2 | 1.5 | 9.3 | 8.2 |
| 2 | 2.5 | 9.3 | 9.3 |
| $2^x$ | 1.5 | 9.3 | 9.3 |

EXAMPLE 8

The other half of the miniboards was dipped into the control agent solutions for 20 seconds. The solutions contained trimethylcoco ammonium chloride and Na-2-ethylhexanoate in different proportions the total active ingredients being 2.5%. The pH was 8.5–10.0. The board were allowed to drip and they were inoculated with the above mentioned spore suspensions of sapstain and mold fungi. The boards were stored at 100% relative humidity (R.H.) at 20° C. They were inspected and visually rated after 3 weeks incubation time. The results presented as the average value of 5 replicate samples are shown in table 1.

The score is:
0—clean
1—some traces of fungal growth
2—several colonies of growing fungi
3—25% of the surface discoloured
4—50% of the surface discoloured The fungal growth on the untreated half of the miniboards scored 4.

EXAMPLE 9

The miniboards treated as in the example 8 were inspected and rated after 5 weeks incubation time at 20° C. and 100% R.H. Results are presented in table 2 as the average score of ten replicate samples.

The results presented in tables 1 and 2 show clearly that the 2.5% a.i. mixtures of trimethyl-coco ammonium chloride and Na-2-ethylhexanoate had synergistic, antifungal effect when the content of trimethylcoco ammonium chloride was 33–67% of the total active ingredients. These mixtures protected the wood even better than 1.5% a.i. technical blend of Na-tetra- and -pentachlorophenoxides, which is a well known antistain chemical.

Trimethylcoco ammonium chloride in 2.5% a.i. solution did not inhibit the mold growth well enough. It also allowed sapstain in some tests. 2.5% a.i. Na-2-ethylhexanoate was quite ineffective in controlling mold and stain fungi.

EXAMPLE 10

The miniboards were treated according to N.T.R. standard 1.4.1.3/79 as in examples 8–9, but that the treatment solutions contained (a) Na-isononanoate (b) Na-iso-octanoate instead of Na-2-ethylhexanoate. The miniboards were inspected and rated after 3 weeks incubation time at 20° C. and 100% R.H. Results are presented in tables 3 and 4 as the average score of ten replicate samples.

EXAMPLE 11

The miniboards were treated as in examples 8–10, but the treatment solutions contained (a) Na-heptanoate (b)

Na-caprinoate (c) Na-caprylate instead of Na-2-ethylhexanoate. The inspection and rating was made as in examples 9–10. Results are presented in tables 5–7 as the average score of ten replicate samples.

Results of mold tests presented in tables 3–4 show clearly that the solutions containing trimethylcoco ammonium chloride and Na-isononanoate performed better than Na-iso-octanoate containing solutions. The synergism with trimethylcoco ammonium chloride was quite obvious in case of Na-isononanoate. The synergism was not as clear in Na-iso-octanoate as well as in straight-chain carboxylates (see tables 5–7) containing mixtures. Anyhow, these treatment solutions gave in any case very good control of sapstain and they performed in mold tests almost as well as the parent quaternary compound trimethylcoco ammonium chloride, especially in 50–67 concentration range. This improves the cost-effectiveness of treatment due to the lower price of the carboxylates in question.

The sapstain control obtained by trimethylcoco ammonium chloride as well as by the Na-carboxylates was clearly poorer, especially in case of the branched-chain carboxylates examined.

TABLE 1

The effectiveness of some anti-sapstain chemicals containing mixtures of quaternary ammonium chlorides and branched chain carboxylic acids as active ingredients.

| The test chemical | | Treatment solution | | Growth of fungi. | | | |
|---|---|---|---|---|---|---|---|
| | | | | Freshly cut pine sapwood(*) | | Water logged pine sapwood | |
| | | % active ingredients | % quaternary compound | Sap-stain | Molds (surface mildew) | Sap-stain | Molds (surface mildew) |
| Trimethylcoco ammonium chloride | pH 8.5–10 | 2.5 | 2.50 | [1.5]3.0 | [1]2.0 | [1.5]3.0 | [6]12 |
| Na—2-ethylhexanoate | pH 8.5–10 | 2.5 | — | [2]20 | 7 | 16 | [5]10 |
| | | | | [2]20 | [2]20 | 9 | [2]4 |
| Trimethylcoco ammonium chloride in mixture with Na—2-ethylhexanoate (33%:67% a.i.) | pH 8.5–10 | 2.5 | 0.82 | 0 | 0 | 0 | [0.5]1.0 |
| | | | | 0 | [0.5]1.0 | 0 | [0.25]0.5 |
| Trimethylcoco ammonium chloride in mixture with Na—2-ethylhexanoate (50%:50%) a.i. | pH 8.5–10 | 2.5 | 1.25 | 0 | 0 | — | — |
| | | | | 0 | 0 | — | — |
| Trimethylcoco ammonium chloride in mixture with Na—2-ethylhexanoate (67%:50%) a.i. | pH 8.5–10 | 2.5 | 1.67 | 0 | 0 | — | — |
| | | | | 0 | [0.5]1.0 | — | — |

(*)according to the N.T.R. standard 1.4.1.3/79

TABLE 2

The long-term effectiveness of some anti-sapstain chemicals containing mixtures of quaternary ammonium chlorides and branched chain carboxylic acids as active ingredients.

| | The test chemical (active ingredients) | | Treatment solution | | | Growth of fungi. | |
|---|---|---|---|---|---|---|---|
| | Trimethylcoco | Na—2-ethyl | | | | Freshly cut pine sapwood | |
| No | ammonium chloride-% | hexanoate - % | pH | % active ingredients | % quaternary compound | Sapstain | Molds (surface mildew) |
| 1 | 0 | 100 | 8.5–10.0 | 2.50 | — | 20 | 20 |
| 2 | 16 | 84 | 8.5–10.0 | 2.50 | 0.40 | 0 | 6.5 |
| 3 | 33 | 67 | 8.5–10.0 | 2.50 | 0.82 | 0 | 3.5 |
| 4 | 50 | 50 | 8.5–10.0 | 2.50 | 1.25 | 0 | 0.5 |
| 5 | 67 | 33 | 8.5–10.0 | 2.50 | 1.67 | 0 | 2 |
| 6 | 84 | 16 | 8.5–10.0 | 2.50 | 2.10 | 0 | 5 |
| 7 | 100 | 0 | 8.5–10.0 | 2.50 | 2.50 | 0 | 5 |
| 8 | The technical blend of Na—chlorophenoxides (tetra-, penta-) | | 11.9 | 1.5 | — | 2.5 | 1 |

EXAMPLE 12

The miniboards were treated as in foregoing examples but the treatment solution contained dioctyldimethylammonium chloride instead of trimethylcocoammonium chloride. The inspection and rating was made as in previous examples with results presented in following table:

| | The test chemical | | | | | | |
|---|---|---|---|---|---|---|---|
| | Dioctyl dimethyl ammonium chloride | Na—2-ethyl-hexanoate | | Treatment solution | | | |
| | | | | % active ingredients | % quaternary compound | Growth of fungi | |
| No | % | % | pH | | | Sapstain | Molds |
| 1 | 100 | 0 | 10 | 2.5 | 2.5 | 1 | 1.5 |
| 2 | 0 | 100 | 10 | 2.5 | — | 10 | 10 |
| 3 | 33 | 67 | 10 | 2.5 | 0.82 | 0 | 0 |
| | | | | 2.0 | 0.66 | 0 | 0 |

Finally, the conclusion can be drawn that trimethylcocoammonium chloride and Na-2-ethylhexanoate form synergistic control agent compositions useful as anti-stain and anti-mould chemicals in sawmill industry. The synergism observed in these compositions is even more obvious in long-term tests and also in tests made with water logged wood, which is normally used in sawmills. The synergism with Na-2-ethylhexanoate has been proved also in case of dodecylbenzyldimethylammonium chloride, dodecylpyridiniumchloride, didecyldimethylammoniumchloride (examples 2, 5, 6) and dioctyldimethylammonium chloride (example 12).

Results obtained with the various carboxylates examined show that the synergism is most obvious in case of Na-2-ethylhexanoate and Na-isononanoate.

Therefore, these salts are more advantageous. Especially, Na-2-ethylhexanoate is the most preferable due to its better water solubility, so that the control agent composition can be produced in more concentrated form. This is more economical. One of the leading ideas of this invention is the water solubility of the product, which should be born in mind.

TABLE 3

The effectiveness of some anti-sapstain chemicals containing mixtures of quaternary ammonium chlorides and branched chain carboxylic acids as active ingredients

| | The test chemical (active ingredients) | | Treatment solution | | | Growth of fungi. Freshly cut pine sapwood | |
|---|---|---|---|---|---|---|---|
| No | Trimethylcoco ammonium chloride-% | Na—isononanoate % | pH | % active ingredients | % quaternary compound | Sapstain | Molds |
| 1 | 0 | 100 | 8.5–10.0 | 2.50 | — | 20 | 20 |
| 2 | 33 | 67 | 8.5–10.0 | 2.50 | 0.82 | 0 | 2 |
| 3 | 50 | 50 | 8.5–10.0 | 2.50 | 1.25 | 0 | — |
| 4 | 67 | 33 | 8.5–10.0 | 2.50 | 1.67 | 0 | 1.5 |
| 5 | 100 | 0 | 8.5–10.0 | 2.50 | 0 | 4 | |
| 6 | The technical blend of Na—chlorophenoxides (tetra-, penta-) | | 11.9 | 1.5 | — | 1 | 0.75 |

TABLE 4

The effectiveness of some anti-sapstain chemicals containing mixtures of quaternary ammonium chlorides and branched chain carboxylic acids as active ingredients

| | The test chemical (active ingredients) | | Treatment solution | | | Growth of fungi. Freshly cut pine sapwood | |
|---|---|---|---|---|---|---|---|
| No | Trimethylcoco ammonium chloride-% | Na—iso-octanoate % | pH | % active ingredients | % quaternary compound | Sapstain | Molds |
| 1 | 0 | 100 | 8.5–10.0 | 2.50 | — | 20 | 20 |
| 2 | 33 | 67 | 8.5–10.0 | 2.50 | 0.82 | 0 | 6 |
| 3 | 50 | 50 | 8.5–10.0 | 2.50 | 1.25 | 0 | 4.5 |
| 4 | 67 | 33 | 8.5–10.0 | 2.50 | 1.67 | 0 | 3.5 |
| 5 | 100 | 0 | 8.5–10.0 | 2.50 | 2.50 | 0 | 4 |
| 6 | The technical blend of Na—chlorophenoxides (tetra-, penta-) | | 11.9 | 1.5 | — | 1 | 0.75 |

TABLE 5

The effectiveness of some anti-sapstain chemicals containing mixtures of quaternary ammonium chlorides and branched chain carboxylic acids as active ingredients

| | The test chemical (active ingredients) | | Treatment solution | | | Growth of fungi. Freshly cut pine sapwood | |
|---|---|---|---|---|---|---|---|
| No | Trimethylcoco ammonium chloride-% | Na—heptanoate % | pH | % active ingredients | % quaternary compound | Sapstain | Molds |
| 1 | 0 | 100 | 8.5–10.0 | 2.50 | — | 7 | 20 |
| 2 | 33 | 67 | 8.5–10.0 | 2.50 | 0.82 | 0 | 8 |
| 3 | 50 | 50 | 8.5–10.0 | 2.50 | 1.25 | 0 | 3 |
| 4 | 67 | 33 | 8.5–10.0 | 2.50 | 1.67 | 0 | 5 |
| 5 | 100 | 0 | 8.5–10.0 | 2.50 | 2.50 | 0 | 4 |
| 6 | The technical blend of Na—chlorophenoxides (tetra-, penta-) | | 11.9 | 1.5 | — | 1 | 0 |

TABLE 6

The effectiveness of some anti-sapstain chemicals containing mixtures of quaternary ammonium chlorides and branched chain carboxylic acids as active ingredients

| | The test chemical (active ingredients) | | Treatment solution | | | Growth of fungi. Freshly cut pine sapwood | |
|---|---|---|---|---|---|---|---|
| No | Trimethylcoco ammonium chloride-% | Na—caprinoate % | pH | % active ingredients | % quaternary compound | Sapstain | Molds |
| 1 | 0 | 100 | 8.5–10.0 | 2.50 | — | 2.5 | 20 |
| 2 | 33 | 67 | 8.5–10.0 | 2.50 | 0.82 | 0 | 12.5 |
| 3 | 50 | 50 | 8.5–10.0 | 2.50 | 1.25 | 0 | 7.5 |
| 4 | 67 | 33 | 8.5–10.0 | 2.50 | 1.67 | 0 | 1 |
| 5 | 100 | 0 | 8.5–10.0 | 2.50 | 2.50 | 0 | 4 |
| 6 | The technical blend of Na—chlorophenoxides (tetra-, penta-) | | 11.9 | 1.5 | — | 1 | 0 |

TABLE 7

The effectiveness of some anti-sapstain chemicals containing mixtures of quaternary ammonium chlorides and branched chain carboxylic acids as active ingredients

| | The test chemical (active ingredients) | | Treatment solution | | | Growth of fungi. Freshly cut pine sapwood | |
|---|---|---|---|---|---|---|---|
| No | Trimethylcoco ammonium chloride-% | Na—caprylate % | pH | % active ingredients | % quaternary compound | Sapstain | Molds |
| 1 | 0 | 100 | 8.5–10.0 | 2.50 | — | 10.5 | 20 |
| 2 | 33 | 67 | 8.5–10.0 | 2.50 | 0.82 | 0 | 11.5 |
| 3 | 50 | 50 | 8.5–10.0 | 2.50 | 1.25 | 0 | 7.5 |
| 4 | 67 | 33 | 8.5–10.0 | 2.50 | 1.67 | 0 | 5 |
| 5 | 100 | 0 | 8.5–10.0 | 2.50 | 2.50 | 0 | 4 |
| 6 | The technical blend of Na—chlorophenoxides (tetra-, penta-) | | 11.9 | 1.5 | — | 2.5 | 0.75 |

What is claimed is:

1. A water-soluble control agent composition for protecting timber, especially sawn timber, against fungi which cause sapstain and mildew, comprising a synergistic mixture consisting essentially of an alkali metal salt of a biocidal organic carboxylic acid selected from the group consisting of 2-ethyl hexanoic acid, isononanoic acid, iso-octanoic acid, heptanoic acid, capric acid and caprylic acid, and trimethylcocoammonium chloride, the weight proportion of said alkali metal salt to said trimethylcocoammonium chloride being in the range of about 33:67 to about 67:33.

2. The control agent composition of claim 1 comprising a synergistic mixture of the sodium salt of isononanoic acid and trimethylcocoammonium chloride.

3. The control agent composition of claim 1 comprising a synergistic mixture of the sodium salt of 2-ethyl hexanoic acid and trimethylcocoammonium chloride.

* * * * *